(12) United States Patent
Hagiya

(10) Patent No.: US 7,973,201 B2
(45) Date of Patent: Jul. 5, 2011

(54) PROCESS FOR PRODUCTION OF HALOGEN-SUBSTITUTED BENZENEDIMETHANOL

(75) Inventor: Koji Hagiya, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 65 days.

(21) Appl. No.: 12/303,585

(22) PCT Filed: Jun. 21, 2007

(86) PCT No.: PCT/JP2007/062951
§ 371 (c)(1),
(2), (4) Date: Dec. 5, 2008

(87) PCT Pub. No.: WO2008/001826
PCT Pub. Date: Jan. 3, 2008

(65) Prior Publication Data
US 2010/0174122 A1  Jul. 8, 2010

(30) Foreign Application Priority Data
Jun. 27, 2006 (JP) .................................. 2006-176479

(51) Int. Cl.
*C07C 33/28* (2006.01)
*C07C 29/136* (2006.01)
(52) U.S. Cl. ........................................ 568/811; 568/814
(58) Field of Classification Search .................. 568/811, 568/814
See application file for complete search history.

(56) References Cited

U.S. PATENT DOCUMENTS
6,759,558 B2 * 7/2004 Rodefeld ...................... 568/811
7,312,366 B2 * 12/2007 Wang et al. ................... 568/811
2007/0055075 A1  3/2007 Wang et al.

FOREIGN PATENT DOCUMENTS
EP  1783108 A1  5/2007
EP  1978008 A1  10/2008
WO  2005/035474 A1  4/2005

OTHER PUBLICATIONS
Edited by The Chemical Society of Japan, 'Shin Jikken Kagaku Koza 15 Sanka to Kangen II' Maruzen Co., Ltd., (Feb. 20, 1977), pp. 216.
Shingeru Oae, Seizo Tamagaki, 'Gosei Kagaku Series Kangen Hanno', Maruzen Co., Ltd., (Jan. 25, 1975), pp. 64.
Edited by kagaku Daijiten Henshu Iinkai, 'Kagaku Dajiten 5', Kyoritsu Shuppan Co., Ltd., (Aug. 15, 1989), pp. 62.

* cited by examiner

*Primary Examiner* — Sikarl A Witherspoon
(74) *Attorney, Agent, or Firm* — Sughrue Mion, PLLC

(57) ABSTRACT

A process for the production of a halogen-substituted benzenedimethanol represented by the formula (2):

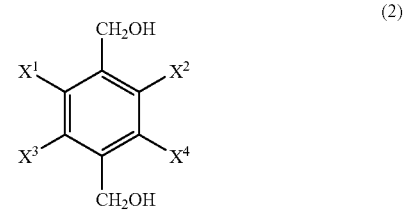

(2)

wherein $X^1$, $X^2$, $X^3$ and $X^4$ are the same or different and independently represent a hydrogen atom or a halogen atom, provided that at least one of $X^1$, $X^2$, $X^3$ and $X^4$ represents a halogen atom, comprising reacting a halogen-substituted terephthalic acid diester represented by the formula (1):

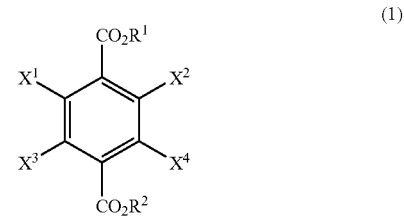

(1)

wherein $X^1$, $X^2$, $X^3$ and $X^4$ are the same meanings as defined above and $R^1$ and $R^2$ are the same or different and independently represent an unsubstituted or substituted alkyl group, a metal borohydride compound and an acid in the presence of an ether solvent, wherein the amount of the acid is 0.2 to 3 moles per 1 mole of the metal borohydride compound based on protons, and the reaction is conducted under the condition where the liquid phase of the reaction mixture is a single layer.

13 Claims, No Drawings

PROCESS FOR PRODUCTION OF HALOGEN-SUBSTITUTED BENZENEDIMETHANOL

TECHNICAL FIELD

The present invention relates to a process for the production of a halogen-substituted benzenedimethanol.

BACKGROUND ART

A halogen-substituted benzenedimethanol is an important compound as raw materials and intermediates of pharmaceuticals and agrichemicals, and especially, U.S. Pat. No. 4,927,852 discloses 2,3,5,6-tetrafluorobenzenedimethanol is useful as an intermediate of household pesticides.

While, for example, a process comprising reducing 2,3,5,6-tetrafluoroterephthalic acid diester using a metal borohydride compound has been known (e.g. CN 1458137 A and WO 2005/035474 A) as a process for the production of the halogen-substituted benzenedimethanol, the development has been desired in the yield.

DISCLOSURE OF THE INVENTION

The present invention provides
<1> A process for the production of a halogen-substituted benzenedimethanol represented by the formula (2):

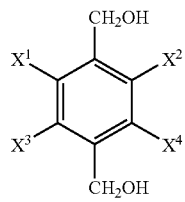

(2)

wherein $X^1$, $X^2$, $X^3$ and $X^4$ are the same or different and independently represent a hydrogen atom or a halogen atom, provided that at least one of $X^1$, $X^2$, $X^3$ and $X^4$ represents a halogen atom, comprising reacting a halogen-substituted terephthalic acid diester represented by the formula (1):

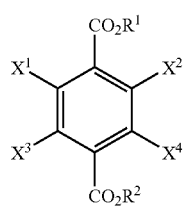

(1)

wherein $X^1$, $X^2$, $X^3$ and $X^4$ are the same meanings as defined above and $R^1$ and $R^2$ are the same or different and independently represent an unsubstituted or substituted alkyl group, a metal borohydride compound and an acid in the presence of an ether solvent, wherein the used amount of the acid is 0.2 to 3 moles per 1 mole of the metal borohydride compound based on protons, and the reaction is conducted under the condition where the liquid phase of the reaction mixture is a single layer;
<2> The process according to <1>, wherein all of $X^1$, $X^2$, $X^3$ and $X^4$ are fluorine atoms;
<3> The process according to <1> or <2>, wherein $R^1$ and $R^2$ are the same and are a C1-C6 alkyl groups in the formula (1);
<4> The process according to any one of <1> to <3>, wherein the reaction is conducted by adding an acid to a mixture containing a halogen-substituted terephthalic acid diester represented by the formula (1), a metal borohydride compound and an ether solvent;
<5> The process according to any one of <1> to <4>, wherein the used amount of the metal borohydride compound is 1 to 3.5 moles per 1 mole of the halogen-substituted terephthalic acid diester represented by the formula (1);
<6> The process according to any one of <1> to <5>, wherein the metal borohydride compound is an alkali metal borohydride;
<7> The process according to <6>, wherein the alkali metal borohydride is sodium borohydride;
<8> The process according to any one of <1> to <7>, wherein the acid is a mineral acid, a carboxylic acid or a sulfonic acid;
<9> The process according to any one of <1> to <7>, wherein the acid is a mineral acid;
<10> The process according to <8> or <9>, wherein the mineral acid is hydrochloric acid or sulfuric acid;
<11> The process according to <8> or <9>, wherein the mineral acid is hydrochloric acid;
<12> The process according to any one of <1> to <11>, wherein the ether solvent is a hydrophilic ether solvent;
<13> The process according to <12>, wherein the hydrophilic ether solvent is tetrahydrofuran, ethylene glycol dimethyl ether or diethylene glycol dimethyl ether.

BEST MODE FOR CARRYING OUT THE PRESENT INVENTION

In the halogen-substituted terephthalic acid diester represented by the formula (1) (hereinafter, simply referred to as the diester (1)), $X^1$, $X^2$, $X^3$ and $X^4$ are the same or different and independently represent a hydrogen atom or a halogen atom, and at least one of $X^1$, $X^2$, $X^3$ and $X^4$ is a halogen atom. Examples of the halogen atom include a fluorine atom, a chlorine atom and a bromine atom, and the fluorine atom is preferable. All of $X^1$, $X^2$, $X^3$ and $X^4$ are more preferably fluorine atoms.

In the formula (1), $R^1$ and $R^2$ are the same or different and independently represent an unsubstituted or substituted alkyl group.

Examples of the unsubstituted alkyl group include a straight chain, branched chain or cyclic C1-C20 alkyl group such as a methyl group, an ethyl group, an n-propyl group, an isopropyl group, an n-butyl group, an isobutyl group, a sec-butyl group, a tert-butyl group, an n-pentyl group, an n-decyl group, a cyclopropyl group, a 2,2-dimethylcyclopropyl group, a cyclopentyl group, a cyclohexyl group and a menthyl group.

Examples of the substituted alkyl group include the alkyl groups wherein at least one hydrogen atom of the above-mentioned unsubstituted alkyl groups is substituted with a substituent.

Examples of the substituent include a fluorine atom; a C1-C6 alkoxy group such as a methoxy group, an ethoxy group, an n-propoxy group, an isopropoxy group, an n-butoxy group, an isobutoxy group, a sec-butoxy group and a tert-butoxy group; a C1-C4 fluorine-substituted alkoxy group such as a trifluoromethoxy group; a C6-C20 aryl group which may be substituted with a C1-C6 alkoxy group such as a phenyl group, a 4-methylphenyl group and a 4-methoxyphenyl group; a C6-C20 aryloxy group which may be substituted with a C1-C6 alkoxy group or a C6-C20 aryloxy group such as a phenoxy group, a 2-methylphenoxy group, a 4-methylphenoxy group, a 4-methoxyphenoxy group and a 3-phenoxyphenoxy group; and a C7-C20 aralkyloxy group which may be substituted with a C1-C6 alkoxy group or a C6-C20 aryloxy group such as a benzyloxy group, a 4-methylbenzyloxy group, a 4-methoxybenzyloxy group and a 3-phenoxybenzyloxy group.

Examples of the substituted alkyl group include a fluoromethyl group, a trifluoromethyl group, a methoxymethyl group, an ethoxymethyl group, a methoxyethyl group and a benzyl group.

As the unsubstituted or substituted alkyl group, a C1-C6 alkyl group is preferable.

Examples of the diester (1) include dimethyl 2-fluoroterephthalate, dimethyl 2-chloroterephthalate, dimethyl 2,5-difluoroterephthalate, dimethyl 2,6-difluoroterephthalate, dimethyl 2,3-difluoroterephthalate, dimethyl 2,5-dichloroterephthalate, dimethyl 2,6-dichloroterephthalate, dimethyl 2,3-dichloroterephthalate, dimethyl 2,3,5-trifluoroterephthalate, dimethyl 2,3,5-trichloroterephthalate, dimethyl 2,3,5,6-tetrafluoroterephthalate, diethyl 2,3,5,6-tetrafluoroterephthalate, di(n-propyl) 2,3,5,6-tetrafluoroterephthalate, diisopropyl 2,3,5,6-tetrafluoroterephthalate, di(n-butyl) 2,3,5,6-tetrafluoroterephthalate, di(tert-butyl) 2,3,5,6-tetrafluoroterephthalate, dimethyl 2,3,5,6-tetrachloroterephthalate, diethyl 2,3,5,5-tetrachloroterephthalate, di(n-propyl) 2,3,5,6-tetrachloroterephthalate, diisopropyl 2,3,5,6-tetrachloroterephthalate, di(n-butyl) 2,3,5,6-tetrachloroterephthalate, di(tert-butyl) 2,3,5,6-tetrachloroterephthalate, di(n-pentyl) 2,3,5,6-tetrachloroterephthalate, di(n-hexyl) 2,3,5,6-tetrachloroterephthalate and dimethyl 2,3,5-trifluoro-6-chloroterephthalate.

The diester (1) can be produced, for example, according to a known method such as a method comprising reacting the corresponding acid halide with the corresponding alcohol compound (e.g. JP 4-66220 B).

Examples of the metal borohydride compound include an alkali metal borohydride such as sodium borohydride, lithium borohydride and potassium borohydride; and an alkaline earth metal borohydride such as calcium borohydride and magnesium borohydride. From the viewpoint of availability, the alkali metal borohydride is preferable and sodium borohydride is more preferable.

While a commercially available borohydride compound is usually used, those prepared according to a known method may be used. For example, sodium borohydride can be prepared easily from a boric acid ester and sodium hydride. Alternatively, other borohydride compounds can be prepared by a reaction of sodium borohydride and the corresponding metal halide, and for example, calcium borohydride is obtained by a reaction of sodium borohydride and calcium chloride. When the borohydride compound is prepared to use, those previously prepared may be added into the reaction system and it may be prepared in the reaction system.

The used amount of the metal borohydride compound is usually 1 mole or more per 1 mole of the diester (1). While there is no specific upper limit, it is practically 3.5 moles or less and preferably 2.5 moles or less from the viewpoint of economic efficiency.

Examples of the ether solvent include diethyl ether, methyl tert-butyl ether, tetrahydrofuran, dioxane, diisopropyl ether, dimethoxyethane, ethylene glycol dimethyl ether and diethylene glycol dimethyl ether. A hydrophilic ether solvent is preferable, and tetrahydrofuran, ethylene glycol dimethyl ether and diethylene glycol dimethyl ether are more preferable and tetrahydrofuran is especially preferable.

While the used amount of the ether solvent is not particularly limited, it is practically 100 parts by weight or less per 1 part by weight of the diester (1) considering volume efficiency.

Alternatively, an organic solvent not inhibiting the reaction other than the ether solvent may be used in combination with the ether solvent. Examples of the organic solvent include an aromatic hydrocarbon solvent such as toluene, xylene and chlorobenzene: and a halogenated hydrocarbon solvent such as chloroform and dichloroethane. The used amount thereof is not particularly limited in so far as it is an amount wherein the liquid phase of the reaction mixture becomes a single layer.

Examples of the acid include a mineral acid such as hydrochloric acid, sulfuric acid and phosphoric acid; an aliphatic carboxylic acid such as formic acid, acetic acid, trifluoroacetic acid, propionic acid, butanoic acid and oxalic acid; an aromatic carboxylic acid such as benzoic acid; an aliphatic sulfonic acid such as methanesulfonic acid, ethanesulfonic acid and trifluoromethanesulfonic acid; and an aromatic sulfonic acid such as benzenesulfonic acid and p-toluenesulfonic acid, and the mineral acid is preferable, and hydrochloric acid and sulfuric acid are more preferable, and hydrochloric acid is especially preferable.

The used amount of the acid is 0.2 to 3 moles and preferably 0.2 to 2.5 moles per 1 mole of the metal borohydride compound based on protons.

When the hydrophilic ether solvent is used as the ether solvent, an aqueous acid solution may be used. The amount of water of the aqueous acid solution may be suitably decided depending on the kinds of the ether solvent, the used amount thereof, the used amount of the diester (1) and the like so that the liquid phase of the reaction mixture will become a single layer without separating to two or more layers. Usually, an aqueous acid solution of which an acid content is 10% by weight or more is used, and an aqueous acid solution of which an acid content is 20 to 90% by weight is preferably used.

The reaction temperature is usually −20 to 120° C., and preferably 10 to 70° C.

The present reaction is conducted by mixing the diester (1), the metal borohydride compound and the acid in the presence of the ether solvent under the condition where the liquid phase of the reaction mixture is a single layer. If the liquid phase is separated to two or more layers, the reaction hardly proceeds and the yield of the desired halogen-substituted benzenedimethanol represented by the formula (2) is low.

When a hydrophobic ether solvent is used as the ether solvent, an acid essentially having no water is used. When a hydrophilic ether solvent is used as the ether solvent, an acid essentially having no water may be used and an acid including water of which amount is within a range capable of keeping the liquid phase of the reaction mixture in a single layer condition may be used.

While the present reaction is usually carried out at normal pressure, it may be carried out under pressure. The progress of the reaction can be checked by a conventional analytical means such as gas chromatography and high performance liquid chromatography.

After completion of the reaction, the halogen-substituted benzenedimethanol represented by the formula (2) can be isolated by mixing the reaction mixture with water or a dilute aqueous mineral acid solution such as hydrochloric acid, sulfuric acid, phosphoric acid and nitric acid, separating the reaction mixture to a two layers of an organic layer and an aqueous layer and then, concentrating the obtained organic layer. The isolated halogen-substituted benzenedimethanol represented by the formula (2) may be further purified by a conventional purification means such as column chromatography.

Examples of thus obtained halogen-substituted benzenedimethanol represented by the formula (2) include 2-fluoro-1,4-benzendimethanol, 2-chloro-1,4-benzendimethanol, 2,5-difluoro-1,4-benzendimethanol, 2,6-difluoro-1,4-benzendimethanol, 2,3-difluoro-1,4-benzendimethanol, 2,5-dichloro-1,4-benzendimethanol, 2,6-dichloro-1,4-benzendimethanol, 2,3-dichloro-1,4-benzendimethanol, 2,3,5-trifluoro-1,4-benzendimethanol, 2,3,5-trichloro-1,4-benzendimethanol, 2,3,5,6-tetrafluorobenzendimethanol, 2,3,5,6-tetrachlorobenzendimethanol and 2,3,5-trifluoro-6-ohlorobenzendimethanol.

EXAMPLES

The present invention will be illustrated in more detail by Examples below. The present invention is not limited to these Examples. The analysis was conducted by high performance liquid chromatography internal standard method.

Example 1

Into a 200 ml flask equipped with a reflux condenser, 9.4 g of sodium borohydride and 100 g of tetrahydrofuran were added at room temperature and a solution obtained by dissolving 28.5 g of dimethyl 2,3,5,6-tetrafluoroterephthalate in 100 g of tetrahydrofuran was added thereto. The obtained mixture was heated to 60° C. and then, 26 g of 35% by weight aqueous hydrochloric acid solution was added dropwise thereto over 5 hours while stirring at the same temperature to effect the reaction for 2 hours at the same temperature. The liquid phase of the reaction mixture was a single layer. After completion of the reaction, the reaction mixture was cooled to room temperature, and 120 g of 5% by weight aqueous hydrochloric acid solution was added thereto to stir followed by leaving at rest to separate to an organic layer and an aqueous layer. The upper organic layer was obtained and 100 g of toluene was added to the obtained organic layer. The obtained solution was washed twice with 30 g of water and then the solvent was distilled away, and 26.0 g of white solids containing 2,3,5,6-tetrafluorobenzenedimethanol was obtained. Purity; 80%, yield: 92%.

Example 2

Into a 200 ml flash equipped with a reflux condenser, 4.6 g of sodium borohydride and 50 g of tetrahydrofuran were added at room temperature and a solution obtained by dissolving 14.7 g of dimethyl 2,3,5,6-tetrafluoroterephthalate in 50 g of tetrahydrofuran was added thereto. The obtained mixture was heated to 60° C. and then, 13 g of 45% by weight aqueous sulfuric acid solution was added dropwise thereto over 5 hours while stirring at the same temperature to effect the reaction for 2 hours at the same temperature. The liquid phase of the reaction mixture was a single layer. After completion of the reaction, the reaction mixture was cooled to room temperature, and 50 g of water was added to the reaction mixture and the resultant mixture was stirred. The mixture was separated to an organic layer and an aqueous layer. The upper organic layer was obtained and 50 g of toluene was added to the obtained organic layer. The obtained solution was washed twice with 30 g of water and then the solvent was distilled away, and 12.4 g of white solids containing 2,3,5,6-tetrafluorobenzenedimethanol was obtained. Purity: 86%, yield: 92%.

Example 3

Into a 200 ml flask equipped with a reflux condenser, 1.6 g of sodium borohydride and 30 g of tetrahydrofuran were added at room temperature and a solution obtained by dissolving 5.1 g of dimethyl 2,3,5,6-tetrafluoroterephthalate in 20 g of tetrahydrofuran was added thereto. To the obtained mixture, a mixed solution of 4.4 g of 35% by weight aqueous hydrochloric acid solution and 6 g of tetrahydrofuran was added dropwise over 5 hours while stirring at room temperature to effect the reaction for 2 hours at 25 to 30° C. The liquid phase of the reaction mixture was a single layer. After completion of the reaction, to the reaction mixture, 30 g of 5% by weight aqueous hydrochloric acid solution was added and the resultant mixture was stirred followed by leaving at rest to separate to an organic layer and an aqueous layer. The upper organic layer was obtained and 50 g of toluene was added to the obtained organic layer. The obtained solution was washed twice with 20 g of water and then the solvent was distilled away, and 4.4 g of white solids containing 2,3,5,6-tetrafluorobenzenedimethanol was obtained. Purity: 85%, yield: 93%.

Example 4

Into a 200 ml flask equipped with a reflux condenser, 1.7 g of sodium borohydride and 30 g of tetrahydrofuran were added at room temperature and a solution obtained by dissolving 5.3 g of dimethyl 2,3,5,6-tetrafluoroterephthalate in 20 g of tetrahydrofuran was added thereto. The obtained mixture was heated to 50° C. and then, a mixed solution of 10.2 g of 35% by weight aqueous hydrochloric acid solution and 10 g of tetrahydrofuran was added dropwise thereto over 5 hours while stirring at the same temperature to effect the reaction for 2 hours at the same temperature. The liquid phase of the reaction mixture was a single layer. After completion of the reaction, the reaction mixture was cooled to room temperature. To the reaction mixture, 30 g of 5% by weight aqueous hydrochloric acid solution was added and the resultant mixture was stirred followed by leaving at rest to separate to an organic layer and an aqueous layer. The upper organic layer was obtained and 50 g of toluene was added to the obtained organic layer. The obtained solution was washed twice with 30 g of water and then the solvent was distilled away, and 4.3 g of white solids containing 2,3,5,6-tetrafluorobenzenedimethanol was obtained. Purity: 89%, yield: 91%.

Example 5

Into a 200 ml flask equipped with a reflux condenser, 1.7 g of sodium borohydride and 30 g of tetrahydrofuran were added at room temperature and a solution obtained by dissolving 5.3 g of dimethyl 2,3,5,6-tetrafluoroterephthalate in 20 g of tetrahydrofuran was added thereto. The obtained mixture was heated to 50° C. and then, a mixed solution of 3 g of acetic acid and 10 g of tetrahydrofuran was added dropwise over 5 hours while stirring at the same temperature to effect the reaction for 2 hours at the same temperature. The liquid phase of the reaction mixture was a single layer. After completion of the reaction, the reaction mixture was cooled to room temperature. To the reaction mixture, 30 g of 5% by weight aqueous hydrochloric acid solution was added and the resultant mixture was stirred followed by leaving at rest to separate to an organic layer and an aqueous layer. The upper organic layer was obtained and 50 g of toluene was added to the obtained organic layer. The obtained solution was washed twice with 30 g of water and then the solvent was distilled away, and 4.1 g of white solids containing 2,3,5,6-tetrafluorobenzenedimethanol was obtained. Purity: 94%, yield: 92%.

Example 6

Into a 50 ml flask equipped with a reflux condenser, 310 mg of sodium borohydride and 7 g of tetrahydrofuran were added at room temperature and 840 mg of dimethyl 2,3,5,6-tetrafluoroterephthalate was added thereto. The obtained mixture was heated to 60° C. and then, a mixed solution of 200 mg of 35% by weight aqueous hydrochloric acid solution and 3 g of tetrahydrofuran was added dropwise thereto over 30 minutes while stirring at the same temperature to effect the reaction for 1 hour at the same temperature. The liquid phase of the reaction mixture was a single layer. After completion of the reaction, the reaction mixture was cooled to room temperature. To the reaction mixture, 4 g of 5% by weight aqueous hydrochloric acid solution was added and the resultant mixture was stirred followed by leaving at rest to separate to an organic layer and an aqueous layer. The upper organic layer was obtained and 2,3,5,6-tetrafluorobenzenedimethanol was contained in the obtained organic layer and the yield thereof was 87%.

Example 7

Into a 100 ml flask equipped with a reflux condenser, 1.6 g of sodium borohydride and 30 g of tetrahydrofuran were added at room temperature and a solution obtained by dissolving 5.1 g of dimethyl 2,3,5,6-tetrafluoroterephthalate in 20 g of tetrahydrofuran was added thereto. The obtained mixture was heated to 50° C. and then, a mixed solution of 2.1 g of 98% by weight sulfuric acid and 10 g of tetrahydrofuran was added dropwise thereto over 6 hours while stirring at the same temperature to effect the reaction for 2 hours at 50 to 55° C. The liquid phase of the reaction mixture was a single layer. After completion of the reaction, the reaction mixture was cooled to room temperature. To the reaction mixture, 30 g of 5% by weight aqueous hydrochloric acid solution was added and the resultant mixture was stirred followed by leaving at rest to separate to an organic layer and an aqueous layer. The upper organic layer was obtained and 50 g of toluene was added to the obtained organic layer. The obtained solution was washed twice with 20 g of water and then the solvent was distilled away, and 3.8 g of white solids containing 2,3,5,6-tetrafluorobenzenedimethanol was obtained. Purity: 82%, yield: 77%.

Comparative Example 1

Into a 200 ml flask, 310 mg of sodium borohydride and 5 g of tetrahydrofuran were added at room temperature and a solution obtained by dissolving 1.0 g of dimethyl 2,3,5,6-tetrafluoroterephthalate in 5 g of tetrahydrofuran was added thereto. The obtained mixture was heated to 65° C. and was stirred to effect the reaction for 6 hours at the same temperature. After completion of the reaction, the reaction mixture was cooled to room temperature. To the reaction mixture, 10 g of 10% by weight aqueous hydrochloric acid solution was added dropwise over 30 minutes at 25 to 30° C. and the obtained mixture was stirred for 1 hour at the same temperature followed by extracting twice with 20 g of ethyl acetate. The obtained organic layer was washed with 10 g of water to obtain a solution containing 2,3,5,6-tetrafluorobenzenedimethanol. Yield: 57%.

Comparative Example 2

Into a 100 ml flask equipped with a reflux condenser, 1.6 g of sodium borohydride and 30 g of tetrahydrofuran were added at room temperature and a solution obtained by dissolving 5.1 g of dimethyl 2,3,5,6-tetrafluoroterephthalate in 20 g of tetrahydrofuran was added thereto. The obtained mixture was heated to 50° C. and then, 30 g of 5% by weight aqueous hydrochloric acid solution was added dropwise thereto over 5 hours while stirring at the same temperature to effect the reaction for 2 hours at the same temperature. The liquid phase of the reaction mixture was separated to two layers. After completion of the reaction, the reaction mixture was left at rest to obtain the upper organic layer. To the obtained organic layer, 50 g of toluene was added. The obtained solution was washed twice with 20 g of water and then the solvent was distilled away, and 3.9 g of white solids containing 2,3,5,6-tetrafluorobenzenedimethanol was obtained. Purity: 47%, yield: 45%.

Comparative Example 3

Into a 200 ml flask equipped with a reflux condenser, 1.7 g of sodium borohydride and 30 g of tetrahydrofuran were added at room temperature and a solution obtained by dissolving 5.3 g of dimethyl 2,3,5,6-tetrafluoroterephthalate in 20 g of tetrahydrofuran was added thereto. To the obtained mixture, a mixed solution of 2.8 g of water and 6 g of tetrahydrofuran was added dropwise over 5 hours while stirring at room temperature to effect the reaction for 2 hours at 25 to 30° C. The liquid phase of the reaction mixture was a single layer. After completion of the reaction, to the reaction mixture, 30 g of 20% by weight aqueous hydrochloric acid solution was added and the resultant mixture was stirred followed by leaving at rest to separate to an organic layer and an aqueous layer. The upper organic layer was obtained and to the obtained organic layer, 50 g of toluene was added. The obtained solution was washed twice with 20 g of water and the solvent was distilled away, and 2.8 g of white solids containing 2,3,5,6-tetrafluorobenzenedimethanol was obtained. Purity: 78%, yield: 52%.

Comparative Example 4

Into a 100 ml flask equipped with a reflux condenser, 0.81 g of sodium borohydride and 15 g of tetrahydrofuran were added at room temperature and a solution obtained by dissolving 2.6 g of dimethyl 2,3,5,6-tetrafluoroterephthalate in 10 g of tetrahydrofuran was added thereto. To the obtained mixture, a mixed solution of 200 mg of 35% by weight aqueous hydrochloric acid solution and 5 g of tetrahydrofuran was added dropwise over 5 hours while stirring at 50° C. to effect the reaction for 2 hours at the same temperature. The liquid phase of the reaction mixture was a single layer. After completion of the reaction, to the reaction mixture, 15 g of 5% by weight aqueous hydrochloric acid solution was added and the resultant mixture was stirred followed by leaving at rest to separate to an organic layer and an aqueous layer. The upper organic layer was obtained and to the obtained organic layer, 20 g of toluene was added. The obtained solution was washed twice: with 10 g of water and the solvent was distilled away, and 1.9 g of brownish yellow solids containing 2,3,5,6-tetrafluorobenzenedimethanol was obtained. Purity: 53%, yield: 49%.

Comparative Example 5

Into a 100 ml flask equipped with a reflux condenser, 0.81 g of sodium borohydride and 15 g of tetrahydrofuran were added at room temperature and a solution obtained by dissolving 2.6 g of dimethyl 2,3,5,6-tetrafluoroterephthalate in 10 g of tetrahydrofuran was added thereto. To the obtained mixture, a mixed solution of 4 g of 86% by weight aqueous sulfuric acid solution and 10 g of tetrahydrofuran was added dropwise over 5 hours while stirring at 50° C. to effect the reaction for 2 hours at the same temperature. The liquid phase of the reaction mixture was a single layer. After completion of the reaction, to the reaction mixture, 20 g of water was added and the resultant mixture was stirred followed by leaving at rest to separate to an organic layer and an aqueous layer. The upper organic layer was obtained and to the obtained organic layer, 20 g of toluene was added. The obtained solution was washed twice with 10 g of water and the solvent was distilled away, and 1.9 g of brownish yellow solids containing 2,3,5,6-tetrafluorobenzenedimethanol was obtained. Purity: 51%, yield: 47%.

INDUSTRIAL APPLICABILITY

According to the present invention, a halogen-substituted benzenedimethanol, which is important as raw materials, intermediates and the like, can be produced in a good yield, and therefore, it is useful industrially.

The invention claimed is:

1. A process for the production of a halogen-substituted benzenedimethanol represented by the forla (2):

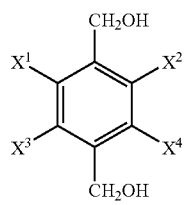

wherein $X^1$, $X^2$, $X^3$ and $X^4$ are the same or different and independently represent a hydrogen atom or a halogen atom, provided that at least one of $X^1$, $X^2$, $X^3$ and $X^4$ represents a halogen atom, comprising reacting a halogen-substituted terephthalic acid diester represented by the formula (1):

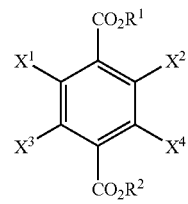

wherein $X^1$, $X^2$, $X^3$ and $X^4$ are the same meanings as defined above and $R^1$ and $R^2$ are the same or different and independently represent an unsubstituted or substituted alkyl group, a metal borohydride compound and an acid in the presence of an ether solvent, wherein the amount of the acid is 0.2 to 3 moles per 1 mole of the metal borohydride compound based on protons, and the reaction is conducted under the condition where the liquid phase of the reaction mixture is a single layer.

2. The process according to claim 1, wherein all of $X^1$, $X^2$, $X^3$ and $X^4$ are fluorine atoms.

3. The process according to claim 1 or 2, wherein $R^1$ and $R^2$ are the same and are a C1-C6 alkyl groups in the formula (1).

4. The process according to claim 1, wherein the reaction is conducted by adding an acid to a mixture containing a halogen-substituted terephthalic acid diester represented by the formula (1), a metal borohydride compound and an ether solvent.

5. The process according to claim 1, wherein the used amount of the metal borohydride compound is 1 to 3.5 moles per 1 mole of the halogen-substituted terephthalic acid diester represented by the formula (1).

6. The process according to claim 1, wherein the metal borohydride compound is an alkali metal borohydride.

7. The process according to claim 6, wherein the alkali metal borohydride is sodium borohydride.

8. The process according to claim 1, wherein the acid is a mineral acid, a carboxylic acid or a sulfonic acid.

9. The process according to claim 1, wherein the acid is a mineral acid.

10. The process according to claim 8 or 9, wherein the mineral acid is hydrochloric acid or sulfuric acid.

11. The process according to claim 8 or 9, wherein the mineral acid is hydrochloric acid.

12. The process according to claim 1, wherein the ether solvent is a hydrophilic ether solvent.

13. The process according to claim 12, wherein the hydrophilic ether solvent is tetrahydrofuran, ethylene glycol dimethyl ether or diethylene glycol dimethyl ether.

* * * * *